United States Patent [19]

Bundy

[11]  4,220,796

[45]  Sep. 2, 1980

[54] 9-DEOXY-9-METHYLENE-5,6-DIDEHYDRO-PGF$_1$ COMPOUNDS

[75] Inventor: Gordon L. Bundy, Portage, Mich.

[73] Assignee: The Upjohn Company, Kalamazoo, Mich.

[21] Appl. No.: 35,144

[22] Filed: May 1, 1979

[51] Int. Cl.$^2$ ............................................ C07C 177/00
[52] U.S. Cl. ............................ 560/121; 260/404; 260/404.5; 260/410; 260/410.5; 260/410.9 R; 260/413; 260/464; 260/465 D; 260/536 A; 260/557 R; 260/559 A; 260/559 R; 260/563 R; 260/570.5 CA; 542/429; 560/19; 560/60; 560/64; 560/106
[58] Field of Search .................... 560/121; 502/503; 260/410, 410.9 R, 413, 410.5, 404, 404.5

[56] References Cited

U.S. PATENT DOCUMENTS 4,060,534  11/1977  Bundy .............................. 260/408

*Primary Examiner*—Robert Gerstl
*Attorney, Agent, or Firm*—Robert A. Armitage

[57] ABSTRACT

The present specification relates to novel 9-deoxy-9-methylene-5,6-trans-didehydro-PGF$_1$ compounds with improved pharmacological properties. While these compounds are useful in inducing a wide variety of prostaglandin-like pharmacological effects, they are specifically useful as regulators of procreation and fertility.

20 Claims, No Drawings

9-DEOXY-9-METHYLENE-5,6-DIDEHYDRO-PGF$_1$ COMPOUNDS

BACKGROUND OF THE INVENTION

The present invention particularly relates to novel 9-deoxy-9-methylene-5,6-trans-didehydro-PGF$_1$-type compounds and methods for their preparation and pharmalogical use.

5,6-trans-didehydro prostaglandins are known in the art. See for example U.S. Pat. Nos. 3,759,978, 3,823,180, 3,832,379 and 3,821,291, which describe the preparation and pharmacological use of such compounds. Moreover, certain 9-deoxy-9-methylene-PGF-type compounds are likewise known in the art, and the preparation and use thereof is described in U.S. Pat. No. 4,060,534. The portion of the specification of the latter patent is incorporated herein by reference for the purpose of describing the manner of preparation and pharmacological use for such compounds.

The naturally-occurring prostaglandins include compounds such as PGF$_{2\alpha}$ and PGE$_2$, depicted by Formulas I and II, respectively. These formulas further indicate the carbon atom numbering for the natural prostaglandins.

5,6-trans-Didehydro-PGF$_{1\alpha}$ represents the geometric isomer of PGF$_{2\alpha}$ wherein the 5,6-cis double bond is isomerized to a 5,6-trans-double bond as indicated in Formula III.

Formula IV provides the chemical structure for 9-deoxy-9-methylene-PGF$_2$, a comound wherein the C-9 hydroxyl of PGF$_{2\alpha}$ is replaced by methylene.

The manner of the depiction of Formulas I–IV herein is the same as that described in U.S. Pat. No. 4,060,534. Moreover, Formulas III–IV depict "prostaglandin analogs", as that term is defined in U.S. Pat. No. 4,060,534. Finally, the various other conventions with respect to nomenclature and the like employed herein are the same as that described in U.S. Pat. No. 4,060,534.

PRIOR ART

Known in the art are certain trans-5,6-didehydro-PG$_1$ compounds and 9-deoxy-9-methylene-PGF compounds, as indicated by the references cited above.

SUMMARY OF THE INVENTION

The present invention particularly provides: a prostaglandin analog of formula V
wherein Y$_1$ is trans—CH=CH—, —C≡C—, —CH$_2$CH$_2$—, or cis—CH=CH—;
wherein M$_1$ is α-R$_5$:α-OH or α-OH:β-R$_5$, wherein R$_5$ is hydrogen or methyl;
wherein L$_1$ is α-R$_3$:β-R$_4$, α-R$_4$:β-R$_3$, or a mixture of α-R$_3$:β-R$_4$ and α-R$_4$:β-R$_3$ wherein R$_3$ and R$_4$ are hydrogen, methyl, or fluoro, being the same or different, with the proviso that one of R$_3$ and R$_4$ is fluoro only when the other is hydrogen or fluoro;
wherein g is 3, 4, or 5;
wherein R$_7$ is
(1) —(CH$_2$)m—CH$_3$, wherein m is an integer from one to 5, inclusive;
(2) phenoxy;
(3) phenoxy substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that R$_7$ is phenoxy or substituted phenoxy, only when R$_3$ and R$_4$ are hydrogen or methyl, being the same or different;
wherein X$_1$ is
(1) —COOR$_1$, wherein R$_1$ is
  (a) hydrogen;
  (b) alkyl of one to 12 carbon atoms, inclusive;
  (c) cycloalkyl of 3 to 10 carbon atoms, inclusive;
  (d) aralkyl of 7 to 12 carbon atoms, inclusive;
  (e) phenyl;
  (f) phenyl substituted with one, two, or three chloro or alkyl of one to 3 carbon atoms;
  (g) phenyl substituted in the para position by
    (i) —NH—CO—R$_{25}$
    (ii) —CO—R$_{26}$
    (iii) —O—CO—R$_{27}$
    (iv) —CH=N—NH—CO—NH$_2$
  wherein R$_{25}$ is methyl, phenyl, acetamidophenyl, benzamidophenyl, or —NH$_2$; R$_{26}$ is hydroxy, methyl, phenyl, —NH$_2$, or methoxy; and R$_{27}$ is phenyl or acetamidophenyl; inclusive, or a pharmacologically acceptable salt thereof when R$_1$ is hydrogen;
(2) —CH$_2$OH;
(3) —COL$_4$, wherein L$_4$ is
  (a) amino of the formula —NR$_{21}$R$_{22}$, wherein R$_{21}$ and R$_{22}$ are
    (i) hydrogen;
    (ii) alkyl or one to 12 carbon atoms, inclusive;
    (iii) cycloalkyl of 3 to 10 carbon atoms, inclusive;
    (iv) aralkyl of 7 to 12 carbon atoms, inclusive;
    (v) phenyl;
    (vi) phenyl substituted with one, 2, or 3 chloro, alkyl of one to three carbon atoms, inclusive, hydroxy, carboxy, alkoxycarbonyl of one to 4 carbon atoms, inclusive, or nitro;
    (vii) carboxyalkyl of 2 to 5 carbon atoms, inclusive;
    (viii) carbamoylalkyl of 2 to 5 carbon atoms, inclusive;
    (ix) cyanoalkyl of 2 to 5 carbon atoms, inclusive;
    (x) acetylalkyl of 3 to 6 carbon atoms, inclusive;
    (xi) benzoylalkyl of 7 to 11 carbon atoms, inclusive;
    (xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
    (xiii) pyridyl;
    (xiv) pyridyl substituted by one, 2, or 3 chloro, alkyl of one to 3 carbon atoms, inclusive, or alkoxy of one to 3 carbon atoms, inclusive;
    (xv) pyridylalkyl of 6 to 9 carbon atoms, inclusive;

(xvi) pyridylalkyl substituted by one, 2, or 3 chloro, alkyl of one to 3 carbon atoms, inclusive, hydroxy or alkoxy of one to 3 carbon atoms, inclusive;

(xvii) hydroxyalkyl of one to 4 carbon atoms, inclusive;

(xviii) dihydroxyalkyl of one to 4 carbon atoms, or (xix) trihydroxyalkyl of one to 4 carbon atoms; with the further proviso that not more than one of $R_{21}$ and $R_{22}$ is other than hydrogen or alkyl;

(b) cycloamino selected from the group consisting of (i) pyrrolidino,
(ii) piperidino,
(iii) morpholino,
(iv) piperazino,
(v) hexamethyleneimino,
(vi) pyrrolino,
(vii) 3,4-didehydropiperidinyl, or
(viii) pyrrolidino, piperidino, morpholino, piperazino, hexamethyleneimino, pyrrolino, or 3,4-didehydropiperidinyl substituted by one or two alkyl of one to 12 carbon atoms, inclusive;

(c) carbonylamino of the formula $-NR_{23}COR_{21}$, wherein $R_{23}$ is hydrogen or alkyl of one to 4 carbon atoms and $R_{21}$ is other than hydrogen, but otherwise as defined above; or (d) sulfonylamino of the formula $-NR_{23}SO_2R_{21}$, wherein $R_{21}$ and $R_{23}$ are as defined in (c);

(4) $-CH_2NL_2L_3$, wherein $L_2$ and $L_3$ are hydrogen or alkyl of one to 4 carbon atoms, inclusive, being the same or different, or a pharmacologically acceptable acid addition salt thereof wherein $X_1$ is $-CH_2NL_2L_3$;

in a pharmaceutical composition consisting essentially of a 5,6-cis isomer of a compound of formula V as the active ingredient thereof, the improvement which comprises:

replacing up to 25% of said 5,6-isomer in said composition with a substantially equal amount by weight of said compound of formula V.

With regard to the divalent substituents described above (e.g., $L_1$ and $M_1$), these divalent radicals are defined as $\alpha\text{-}R_i\text{:}\beta\text{-}R_j$, wherein $R_i$ represents the substituent of the divalent moiety in the alpha configuration with respect to the ring and $R_j$ represents the substituent of the divalent moiety in the beta configuration with respect to the plane of the ring. Accordingly, when $M_1$ is defined as $\alpha\text{-}OH\text{:}\beta\text{-}R_5$, the hydroxy of the $M_1$ moiety is in the alpha configuration, i.e., as in $PGF_{2\alpha}$ above, and the $R_5$ substituent is in the beta configuration. Not all carbon atoms to which such divalent moieties are attached represent asymmetric centers. For example when both valence bonds are to hydrogen (e.g., $L_1$ is $\alpha\text{-H:}\beta\text{-H}$), then no asymmetric center is present.

All novel prostaglandin analogs herein are named as 9-deoxy-9-methylene-5,6-trans-didehydro-$PGF_1$ compounds by virtue of the substitution of methylene for hydroxy at C-9 and the 5,6-trans unsaturation in the C-8 side chain.

When $R_5$ is methyl, the prostaglandin analogs are all named as "15-methyl-PG" compounds. Further, except for compounds wherein $Y_1$ is cis—CH=CH—, compounds wherein the $M_1$ moiety contains an hydroxyl in the beta configuration are additionally named as 15-epi-PG compounds. For the compounds wherein $Y_1$ is cis-CH=CH—, then only compounds wherein the $M_1$ moiety contains an hydroxyl in the alpha configuration are named as 15-epi-PG compounds. For a description of this convention of nomenclature for identifying C-15 epimers, see U.S. Pat. No. 4,016,184, issued Apr. 5, 1977, particularly columns 24–27 thereof.

When g is 4 or 5, the prostaglandin analogs so described are "2a-homo" or "2a,2b-dihomo" compounds, since in this event the $X_1$ terminated side chain contains 8 or 9 carbon atoms, respectively, in place of the 7 carbon atoms contained in $PGF_{2\alpha}$. These additional carbon atoms are considered as though they were inserted between the C-2 and C-3 positions. Accordingly, these additional carbon atoms are referred to as C-2a and C-2b, counting from the C-2 to the C-3 position.

The novel prostaglandin analogs herein which contain $-(CH_2)_2-$, cis—CH=CH—, or $-C\equiv C-$ as the $Y_1$ moiety, are accordingly referred to as "13,14-dihydro", "cis-13", or "13,14-didehydro" compounds, respectively.

When $R_7$ is $-(CH_2)_m-CH_3$, wherein m is as defined above, the compounds so described are named as "19,20-dinor", "20-nor", 20-methyl" or "20-ethyl" compounds when m is one, 2, 4, or 5, respectively.

When $R_7$ is phenyl and neither $R_3$ nor $R_4$ is methyl, the compounds so described are named as "16-phenyl-17,18,19,20-tetranor" compounds, when s is zero. When $R_7$ is substituted phenyl, the corresponding compounds are named as "16-(substituted phenyl)-17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenyl or 16-(substituted phenyl)-18,19,20-trinor" compounds or "16-methyl-16phenyl- or 16-(substituted phenyl)-18,19,20-trinor" compounds, respectively.

When $R_7$ is phenylmethyl, the compounds so described are named as "17-phenyl-18,19,20-trinor" compounds. When $R_7$ is substituted phenylmethyl the corresponding compounds are named as "17-(substituted phenyl)-18,19,20-trinor" compounds.

When $R_7$ is phenylethyl the compounds so described as named as "18-phenyl-19,20-dinor" compounds, when s is 0. When s is one, 2, or 3, the corresponding compounds are named as "18-(substituted phenyl)-19,20-dinor" compounds.

When $R_7$ is phenylpropyl, the compounds so described are named as "19-phenyl-20-nor" compounds. When $R_7$ is substituted phenylpropyl the corresponding compounds are named as 19-(substituted phenyl)-20-nor" compounds.

When $R_7$ is phenoxy and neither $R_3$ nor $R_4$ is methyl, the compounds so described are named as "16-phenoxy-17,18,19,20-tetranor" compounds. When $R_7$ is substituted phenoxy the corresponding compounds are named as "16-(substituted phenoxy)-17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenoxy or 16-(substituted phenoxy)-18,19,20-trinor" compounds or "16-methyl-16-phenoxy- or 16-(substituted phenoxy)-18,19,20-trinor" compounds, respectively.

When at least one of $R_3$ and $R_4$ is not hydrogen then (except for the 16-phenoxy or 16-phenyl compounds discussed above) there are described the "16-methyl" (one and only one of $R_3$ and $R_4$ is methyl), "16,16-dimethyl" ($R_3$ and $R_4$ are both methyl), "16-fluoro"

(one and only one of $R_3$ and $R_4$ is fluoro), "16,16-difluoro" ($R_3$ and $R_4$ are both fluoro) compounds. For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When $X_1$ is —$CH_2OH$, the compounds so described are named as "2-decarboxy-2-hydroxymethyl" compounds.

When $X_1$ is —$CH_2NL_2L_3$, the compounds so described are named as "2-decarboxy-2-aminomethyl" or "2-(substituted amino)methyl" compounds.

When $X_1$ is —$COL_4$, the novel compounds herein are named as PG-type, amides. Further, when $X_1$ is —$COOR_1$, the novel compounds herein are named as PG-type, esters and PG-type, salts.

Examples of phenyl esters substituted in the para position (i.e., $X_1$ is —$COOR_1$, $R_1$ is p-substituted phenyl) include p-acetamidophenyl ester, p-benzamidophenyl ester, p-(p-acetamidobenzamido)phenyl ester, p-(p-benzamidobenzamido)phenyl ester, p-carboxyphenyl ester, p-amidocarbonylamiophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)-phenyl ester, and p-hydroxybenzaldehyde semicarbazone ester.

Examples of novel amides herein (i.e., $X_1$ is —$COL_4$) include the following:

(1) Amides within the scope of alkylamino groups of the formula —$NR_{21}R_{22}$ are methylamide, ethylamide, n-propylamide, n-butylamide, n-pentylamide, n-hexylamide, n-heptylamide, n-octylamide, n-nonylamide, n-decylamide, n-undecylamide, and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-Ncyclopentylamide, N-methyl-N-cyclohexylamide, N-ethyl-Ncyclopentylamide, and N-ethyl-N-cyclohexylamide. Amides within the scope of aralkylamino are benzylamide, 2-phenylethylamide, 2-phenylethylamide, and N-methyl-N-benzylamide. Amides within the scope of substituted phenylamido are p-chloroanilide, N-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methylanilide, p-ethylanilide, t-butylanilide, p-carboxyanilide, p-methoxycarbonylanilide, o-carboxyanilide and o-hydroxyanilide. Amides within the scope of carboxyalkylamino are carboxymethylamide, carboxyethylamide, carboxypropylamide, and carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxybenzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5-trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlroobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutylamide, m-methylbenzoylbutylamide, p-ethylbenzoylbutylamide, m-methylbenzoylbutylamide, p-ethylbenzoylbutylamide, t-butylbenzoylbutylamide, p-carboxybenzoylbutylamide, m-methoxycarbonaylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methylα-pyridylamide, 4-methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloro-α-pyridylmethylamide, 4-chloro-β-pyridylmethylamide, 4-methyl-α-pyridylpropylamide, 4-methyl-β-pyridylpropylamide, 4-chloro-α-pyridylpropylamide, 4-chloro-β-pyridylpropylamide, 4-methyl-α-pyridylbutylamide, 4-methyl-β-pyridylbutylamide, 4-chloro-α-pyridylbutylamide, 4-chloro-β-pyridylbutylamide, 4-methyl-β-pyridylbutylamide. Amides within the scope of hydroxyalkylamino are hydroxymethylamide, α-hydroxyethylamide, β-hydroxyethylamide, α-hydroxypropylamide, β-hydroxypropylamide, γ-hydroxypropylamide, 1-(hydroxymethyl)ethylamide, 1-(hydroxymethyl)propylamide, (2-hydroxymethyl)propylamide, and α,α-dimethyl-β-hydroxyethylamide. Amides within the scope of dihydroxyalkylamino are dihydroxymethylamide, α,α-dihydroxyethylamide, α,β-dihydroxyethylamide, β,β-dihydroxyethylamide, α,α-dihydroxypropylamide, α,β-dihydroxypropylamide, α,γ-dihydroxypropylamide, β,β-dihydroxypropylamide, β,γ-dihydroxypropylamide, γ,γ-dihydroxypropylamide, 1-(hydroxymethyl)2-hydroxymethylamide, 1-(hydroxymethyl)-1-hydroxyethylamide, α,α-dihydroxybutylamide, α,β-dihydroxybutylamide, α,γ-dihydroxybutylamide, α,δ-dihydroxybutylamide, β,β-dihydroxybutylamide, β,γ-dihydroxybutylamide, β,δ-dihydroxybutylamide, γ,γ-dihydroxybutylamide, γ,δ-didihydroxybutylamide, δ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of cyclamino groups described above are pyrrolidylamide, piperidylamide, morpholinylamide, hexamethyleneiminylamide, piperazinylamide, pyrrolinylamide, and 3,4-didehydropiperidinylamide.

(3) Amides within the scope of carbonylamino of the formula $-NR_{23}COR_{21}$ are methylcarbonylamide, ethylcarbonylamide, phenylcarbonylamide, and benzylcarbonylamide.

(4) Amides within the scope of sulfonylamino of the formula $-NR_{23}SO_2R_{21}$ are methylsulfonylamide, ethylsulfonylamide, phenylsulfonylamide, p-tolylsulfonylamide, benzylsulfonylamide.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tertbutylphenyl, 2,5-dimethylphenyl, 4-chloro-2-methylphenyl, and 2,4-dichloro-3-methylphenyl.

Examples of substituted phenoxy, phenylmethyl, phenylethyl, or phenylpropyl of the $R_7$ moiety are (o-, m-, or p-)tolyl, (o-, m-, or p-(ethylphenyl, 2-ethyltolyl, 4-ethyl-o-tolyl, 5-ethyl-m-tolyl, (o-, m-, or p-)propylphenyl), 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-,4-,5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3- or 4-(chloro-2-fluorophenyl, (o-, m-, or p-)trifluoromethylphenyl, (o-, m-, or p-)methoxyphenyl, (o-, m-, or p-)ethoxyphenyl, (4- or 5-)chloro-2-methoxyphenyl, 2,4-dichloro-(4- or 6-)methylphenyl, (o-, m-, or p-)tolyloxy, (o-, m-, or p-)ethylphenyloxy, 2-ethyltolyloxy, 4-ethyl-o-tolyloxy, 5-ethyl-m-tolyloxy, (o-, m-, or p-)propylphenoxy, 2-propyl-(o-, m-, or p-)tolyloxy, 4-isopropyl-2,6-xylyloxy, 3-propyl-4-ethylphenyloxy, (2,3,4-, 2,3,5-, 2,3,6-, or 2,4,5-)trimethylphenoxy, (o-, m-, or p-)fluorophenoxy, 2-dluoro-(o-, m-, or p-)tolyloxy, 4-fluoro-2,5-xylyloxy, (2,4-, 2,5-, 2,6-, 3,4-, or 3,5-)difluorophenoxy, (o-, m-, or p-)-chlorophenoxy, 2-chloro-p-tolyloxy, (3,4,5, or 6-)chloro-o-tolyloxy, 4-chloro-2-propylphenoxy, 2-isopropyl-4-chlorophenoxy, 4-chloro-3,5-xylyloxy, (2,3-, 2,4-, 2,5-, 2,6-, 3,4-, or 3,5-)dichlorophenyloxy, 4-chloro-3-fluorophenoxy, (3- or 4-)chloro-2-fluorophenoxy, (o-, m-, or p-)trifluoromethylphenoxy, (o-, m-, or p-)methoxyphenoxy, (o-, m-, or p-)ethoxyphenoxy, (4- or 5-)chloro-2-methoxyphenoxy, 2,4-dichloro-(5- or 6-)methylphenoxy, (o-, m-, or p-)tolylmethyl, (o-, m-, or p-)ethylphenylmethyl, 2-ethyltolylmethyl, 4-ethyl-o-tolylmethyl, 5-ethyl-m-tolylmethyl, (o-, m-, or p-)(propylphenylmethyl, 2-propyl-(o-, m-, or p-)tolylmethyl, 4-isopropyl-2,6-xylylmethyl, 3-propyl-4-ethylphenylmethyl, (2,3,4-, 2,3,5-, 2,3,6-, or 2,3,5-)trimethylphenylmethyl, (o-, m-, or p-)fluorophenylmethyl, 2-fluoro-(o-, m-, or p-)tolylmethyl, 4-fluoro-2,5-xylylmethyl, (2,4-, 2,5-, 2,6-, 3,4-, or 3,5-)difluorophenyl, (o-, m-, or p-)chlorophenylmethyl, 2-chloro-p-tolylmethyl, (3,4,5, or 6-)chloro-o-tolylmethyl, 4-chloro-2-propylphenylmethyl, 2-isopropyl-4-chlorophenylmethyl, 4-chloro-3,5-xylylmethyl, (2,3-, 2,4-, 2,5-, 2,6-, 3,4-, or 3,5-)dichlorophenylmethyl, 4-chloro-3-fluorophenylmethyl, (3- or 4-)chloro-2-fluorophenylmethyl, (o-, m-, or p-)trifluoromethylphenylmethyl, (o-, m-, or p-)methoxyphenylmethyl, (o-, m-, or p-)ethoxyphenylmethyl, (4- or 5-)chloro-2-methoxyphenylmethyl, and 2,4-dichloro-(4- or 6-)methoxyphenylmethyl.

The novel prostaglandin analogs described above are surprisingly and unexpectedly useful for the same purposes and in the same manner as the corresponding 9-deoxy-9-methylene-PGF$_2$-type compounds described in U.S. Pat. No. 4,060,534.

Accordingly the novel 9-deoxy-9-methylene-5,6-trans-didehydro-PGF$_1$ compounds herein are useful in pharmaceutical compositions either as a sole active ingredient or in pharmaceutical compositions in accordance with the present invention which contain mixtures of these novel compounds together with the prior art 9-deoxy-9-methylene-PGF$_2$ compounds of the 5,6-cis configuration.

The composition for pharmaceutical use are all prepared as is known in the art for the pharmaceutical composition of the 9-deoxy-9-methylene-PGF$_1$ compounds of U.S. Pat. No. 4,060,534, incorporated here by reference.

An especially important application of the novel compounds of the present invention reside in the regulation of procreation and fertility. Accordingly, these compounds are especially useful as regulators of the menstrual cycle, regulators of the estrous cycle, abortifacients, or labor inducers. When used for these purposes, U.S. Pat. No. 4,060,534 provides a general description of the manner of use.

With regard to the novel prostaglandin analogs disclosed herein, certain compounds are preferred in that they exhibit increased potency and/or selectivity of action. Among the prefered prostaglandin analogs in accordance with the present invention are those wherein Y$_1$ is trans—CH=CH—. Further preferred are compounds wherein R$_3$ and R$_4$ are the same. Likewise, when R$_5$ is methyl, preferred compounds herein are those wherein R$_3$ and R$_4$ are both hydrogen. When at least one of R$_3$ and R$_4$ is not hydrogen, however, the preferred compounds herein are those wherein R$_5$ is hydrogen.

Compounds containing 7 and only 7 carbon atoms in the C-8 side chain are preferred. Thus, the preferred prostaglandin analogs herein are those wherein g is 3.

With respect to R$_7$, preferred compounds herein are those wherein m is 3.

With regard to the carboxylic acid and esters, preferred compounds herein are those wherein R$_1$ is hydrogen, alkyl of one to 4 carbon atoms, inclusive, or a pharmacologically acceptable cation. Among the esters, further preferred compounds are those wherein R$_1$ is methyl or ethyl, most preferably being methyl.

Among the 2-decarboxy-2-aminomethyl-9-deoxy-9-methylene-5,6-trans-didehydro-PGF$_1$ compounds described herein, preferred compounds are those wherein L$_2$ and L$_3$ are both hydrogen.

When X$_1$ is —COOR$_1$, the novel PG analogs so described are used for the purposes described above in the free acid form, in ester form, in pharmacologically acceptable salt form. When the ester form is used, the ester is any of those within the above definition of R$_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel prostaglandin analogs of this invention for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereto, e.g., 1-methylpiperidine, 4-ethylmorpholine, 1-isopropylpyrrolidine, 2-methylpyrrolidine, 1,4-dimethylpiperazine, 2-methylpiperidine, and the like as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like. Further useful amine salts of the basis amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

When X$_1$ is —CH$_2$NL$_2$L$_3$, the novel PG analogs so described are used for the purposes described above in either free base or pharmacologically acceptable acid addition salt form.

The acid addition salts of the 2-decarboxy-2-aminomethyl- or 2-(substituted aminomethyl)-PG analogs provided by this invention, are the hydrochlorides, hydrobromides, hydriodides, sulfates, phosphates, cyclohexanesulfamates, methanesulfonates, ethanesulfonates, benzenesulfonates, toluenesulfonates and the like, prepared by reacting the PG analog with the stoichiometric amount of the acid corresponding to the pharmacologically acceptable acid addition salt.

The novel 9-deoxy-9-methylene-5,6-trans-didehydro-PGF$_1$ compounds are conveniently prepared by a number of readily available chemical techniques, the most important of which is by photochemical isomerization of the corresponding 5,6-cis isomer, i.e., the 9-deoxy-9-methylene-PGF$_2$ compound. These 5,6-cis compounds are prepared in the art by methods described in U.S. Pat. No. 4,060,534. The photochemical isomerization reaction proceeds by methods known in the art, particularly those described by Moussebois, C., et al., J. Chem. Soc. (C) 260 (1966), which employs the use of UV radiation (3500 Angstroms) in diphenyl disulfide and benzene.

Once the photochemical isomerization reaction is complete, the equillibrium mixture of trans and cis isomers is separated by conventional means preferably silver nitrate-impregnated silica gel silica gel chromatography. The novel 9-deoxy-9-methylene-5,6-transdidehydro-PGF$_1$ compounds are preferably prepared in the form of their lower alkyl esters (X$_1$ is —COOR$_1$ and R$_1$ is alkyl), and chromatography preferably takes place on silver nitrate impregnated silica gel.

Alternatively, methods described in U.S. Pat. No. 4,060,534 for the production of the 9-deoxy-9-methylene-PGF$_2$ compounds (the 5,6-cis isomers) may be modified to yield a mixture of the novel trans-isomers herein and the prior art cis-isomers. Particularly, the trans isomers produced by prolonged exposure to thiophenol. Such a prolonged exposure to thiophenol results when the aluminum amalgum reduction described in the preparation of the prior art 5,6-cis isomer is not immediately followed by purification of the product thusly obtained. By varying in the interval between the aluminum amalgum reduction and the subsequent purification of the 9-deoxy-9-methylene-PGF-type product, varying mixtures of isomers are obtained.

In the industrial scale production of the 5,6-cis isomer, prolonged exposure time to thiophenol is ordinarily experienced. Thus, the industrial scale production of 5,6-cis isomer occasions the production of mixtures containing appreciable quantities, e.g., typically about 5-25% of the novel 9-deoxy-9-methylene-5,6-trans-didehydro-PGF$_1$ compounds. When the novel pharmaceutical compositions of the present invention are employed, however, the chromatographic separation of these two isomers need not be undertaken in order to obtain pharmaceutically acceptable compositions for the therapeutic indications heretofore known for the 9-deoxy-9methylene-PGF$_2$ compounds of the 5,6-cis configuration. Accordingly, the novel pharmaceutical compositions provided by the present invention represent a surprising and unexpected improvement over the prior art compositions, i.e., U.S. Pat. No. 4,060,534, inasmuch as these novel compositions containing a mixture of active substances are more economically prepared in industrial scale amounts, while maintaining pharmacological efficacy.

In accordance with the present invention there are, therefore, provided pharmaceutical compositions in unit dosage form whose active ingredients are substantially equal in weight to the weight of the 5,6-cis isomer contained in the prior art compositions of U.S. Pat. No. 4,060,534. Thus, depending upon the particular indication and the exact ratio of the cis- and trans-isomers in the composition, the total weight of active ingredients in the unit dose will vary by not more than 20% from the weight of the active ingredient in these prior art compositions.

An especially useful embodiment of the present invention are the novel compositions herein which contain less than 5% of the novel 9-deoxy-9-methylene-5,6-transdidehydro-PGF$_1$ compound. Such compositions, containing a relatively small amount of the novel trans-isomer, are surprisingly and unexpectedly substantially equivalent in pharmacological terms to the 9-deoxy-9-methylene-PGF$_2$ compositions known in the prior art, and are advantageously prepared by avoiding the difficult and realtively uneconomic separation of the isomeric mixture resultant from the large-scale production thereof.

DESCRIPTION OF THE PREFERRED EMBODIMENTS

EXAMPLE 1

9-Deoxy-9-methylene-5,6-trans-didehydro-PGF$_1$.

Following the procedure of Example 8 of U.S. Pat. No. 4,060,534, but at a scale 10,000 times larger than described therein there is obtained first a mixture of 9-deoxy-9-methylene-PGF$_2$, methyl ester, and 9-deoxy-9-methylene-5,6-didehydro-PGF$_1$, methyl ester. Silica gel TLC R$_f$ for these compounds is, respectively, 0.25 and 0.31 in the A-IX solvent system (silver nitrate impregnated plates), Hamberg, M., et al., J. Biol. Chem. 241:257 (1966).

Chromatographic separation of these methyl esters on acid-washed silica gel yields pure 9-deoxy-9-methylene-5,6-trans-didehydro-PGF$_1$, methyl ester. Saponification of the methyl ester to the corresponding free acid following the procedure of Example 8, Part C of U.S. Pat. No. 4,060,534 yields title product.

EXAMPLE 2

9-Deoxy-9-methylene-trans-5,6-didehydro-16,16-dimethyl-PGF$_1$

A solution of 20 mg of 9-deoxy-9-methylene-16,16-dimethyl-PGF$_2$ (Example 9, U.S. Pat. No. 4,060,534) and 20 mg of diphenyl disulfide in 20 ml of benzene is irradiated at 3500 Angstroms at 10° C. (water cooling) under nitrogen atmosphere with stirring. After about 2 hr, a ratio of cis- to trans-isomers of 1:1 was obtained and the resulting mixture concentrated under reduced pressure and chromatographed on 5 g of acid-washed silica gel, eluting with ethyl acetate and hexane (1:1) and thereafter with ethyl acetate alone. 12 g of pure 9-deoxy-9-methylene-5,6-trans-didehydro-PGF$_1$ were obtained. Silica gel TLC R$_f$ is 0.31 in ethyl acetate, hexane, and acetic acid (45:55:0.5); 0.27 in acetone, methylene chloride, and acetic acid (35:65:0.5); and 0.33 in the A-IX solvent system (silver nitrate impregnated plate). Infrared absorptions are observed at 3400, 3080, 2660, 1710, 1660, 1440, 1365, 1235, 1075, 1015, 1000, and 885 cm$^{-1}$. NMR absorptions are observed at 6.00, 5.75-5.25, 5.05-4.8, 4.05-3.55, 0.88, and 0.85δ. The mass spectrum for the trimethylsilyl derivatives exhibits a weak molecular ion at 594, a high resolution peak at 579.3689, and other peaks at 504, 495, 489, 405, 379, 315, and 243.

EXAMPLE 3

9-Deoxy-9-methylene-5,6-trans-didehydro-16-phenoxy-17,18,19,20-tetranor-PGF$_1$, methyl ester A. A solution of 4.0 g of 16-phenoxy-17,18,19,20-tetranor-PGF$_{2\alpha}$, 11,15-bis(tetrahydropyranyl ether) in 100 ml of acetonitrile was treated with 7.5 ml of diisopropylethylamine, followed by treatment with 15 ml of methyl iodide. The resulting solution is then stirred at ambient temperature for 3 hr, poured into ice and brine, extracted with ethyl acetate, washed successively with water, aqueous sodium bisulfate, and brine, dried over sodium sulfate and concentrated under reduced pressure to a residue (3.8 g) of 16-phenoxy-17,18,19,20-tetranor-PGF$_{2\alpha}$, methyl ester. 11,15-bis(tetrahydropyranyl ether).

B. To a solution at −20° C. of 3.8 g of the reaction product of Part A in 200 ml of acetone is added (dropwise) 3 ml of Jones reagent, Bowden, K., et al., J. Chem.

Soc. 39 (1946). The resulting mixture is then stirred at −15° C. for 10 min, at which time the reaction is quenched by addition of 1 ml of isopropyl alcohol. After stirring for an additional 15 min, the resulting mixture is then poured into ice and water, extracted with ethyl acetate, washed with water, aqueous sodium bicarbonate, and brine, dried over anhydrous sodium sulfate, and concentrated under reduced pressure to a residue (3.63 g). Chromatography on 350 g of silica gel packed with acetone and methylene chloride (3:97) and eluted with 3–5% acetone in methylene chloride yields pure 16-phenoxy-17,18,19,20-tetranor-PGE$_2$, methyl ester, 11,15-bis(tetrahydropyranyl ether), 2.8 g. Silica gel TLC R$_f$ is 0.5 in acetone and methylene chloride (1:19).

C. Under a nitrogen atmosphere with exclusion of moisture, 2.52 g of methylphenyl-N-methylsulfoximine in 30 ml of tetrahydrofuran is cooled to 0° C. and treated with 4.9 ml of 3 M methylmagnesium chloride in tetrahydrofuran. After 15 min at 0° C., the sulfoximine-containing solution is cooled to −78° C. and added over 15 min to a stirred solution (−78° C.) of the reaction product of Part B (2.8 g) in 15 ml of tetrahydrofuran. The reaction mixture is stirred for 1 hr at −78° C., then stirred into an ice-saturated ammonium chloride-water solution, extracted with ethyl acetate, washed successively with sodium bicarbonate and brine, dried over anhydrous sodium sulfate, and concentrated under reduced pressure to a residue, 3.67 g. This residue is then dissolved in a mixture of 12 ml of tetrahydrofuran, 24 ml of water, and 60 ml of acetic acid. After stirring for 18 hrs at 35° C., the reaction mixture is then poured into brine, extracted over ethyl acetate, washed successively with brine, aqueous sodium bicarbonate, and brine, dried over anhydrous sodium sulfate, and concentrated under reduced pressure to a residue, 4.9 g. This residue in 160 mg of tetrahydrofuran, 24 ml of water, and 24 ml of acetic acid is added at 15° C. to aluminum amalgam made from 5.25 g of 20 mesh aluminum metal. After vigourous stirring for 2 hr, the resulting mixture is diluted with ethyl acetate and diatomaceous earth is added. The mixture is then filtered through diatomaceous earth and the filtrate, including ethyl acetate washes, is washed with brine, 10% aqueous potassium carbonate and brine, dried over anhydrous sodium sulfate, and concentrated under reduced pressure to a residue, 2.9 g. This residue is then dissolved in 10 ml of tetrahydroguran, 24 ml of water, and 60 ml of acetic acid and stirred for 18 hr at 22° C. The resulting mixture is then poured into brine and extracted with ethyl acetate. The ethyl acetate extracts are then washed with brine, aqueous sodium bicarbonate, and brine, dried over magnesium sulfate, and concentrated under reduced pressure to a residue (2.9 g). Chromatographing on 350 g of silica gel packed with 50% ethyl acetate in hexane and eluted with 50–70% ethyl acetate in hexane yields 683 g of a mixture of 5,6-cis- and 5,6-transisomers.

Chromatography on 250 g of silver nitrate-impregnated silica gel packed with acetonitrile and with 50 g of silver nitrate and eluted with ethyl acetate and hexane yields 264 mg of pure title product, 9-deoxy-9-methylene-5,6-trans-16-phenoxy-17,18,19,20-tetranor-PGF$_2$, methyl ester.

EXAMPLE 4

9-Deoxy-9-methylene-5,6-trans-didehydro-16-phenoxy-17,18,19,20-tetranor-PGF$_2$

At 0° C. a stirred solution of 264 mg of the title product of Example 3 in 5 ml of methanol is treated, under a nitrogen atmosphere, with 5 ml of 2 M aqueous potassium hydroxide. The resulting solution is then stirred at ambient temperature for 2 hr, poured into brine, acidified with 5.5 ml of 2 M aqueous potassium bisulfate, and extracted with ethyl acetate. The organic extracts are then washed with brine, dried over sodium sulfate, and concentrated under reduced pressure to yield 152 g of pure title product. Silica gel TLC R$_f$ is 0.53 in acetone, hexane, and acetic acid (60:40:1) and 0.30 in methanol, acetic acid, and chloroform (10:10:80; silver nitrate-impregnated plate). Infrared absorptions are observed at 3350, 2620, 1710, 1655, 1600, 1585, 1495, 1245, 1075, 1040, 970, 885, 755, and 690 cm$^{-1}$.

The mass spectrum exhibits a weak molecular ion at 602 and a high resolution peak of 587.3016 and other peaks at 512, 508, 495, 405, and 315.

In accordance with the above Examples, there are prepared the novel 9-deoxy-9-methylene-5,6-trans-didehydro-PGF compounds of the instant invention and the novel pharmaceutical compositions herein containing mixtures of 5,6-cis and novel 5,6-trans isomers.

Further, following the procedure of the above examples, there are prepared the various 5,6-trans-didehydro-9-deoxy-9-methylene-PGF-type compounds of Formula V free acid or methyl ester form which exhibit the following side chain characteristics:

15-methyl-;
16-methyl-;
16,16-dimethyl-;
16-fluoro-;
16,16-difluoro-;
15-methyl-16,16-difluoro-;
17-phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-methyl-17-phenyl-18,19,20-trinor-;
16-methyl-17-phenyl-18,19,20-trinor-;
16,16-dimethyl-17-phenyl-18,19,20-trinor-;
16-fluoro-17-phenyl-18,19,20-trinor-;
16,16-difluoro-17-phenyl-18,19,20-trinor-;
16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
15-methyl-16-phenoxy-17,18,19,20-tetranor-;
16-phenoxy-18,19,20-trinor-;
15-methyl-16-phenoxy-18,19,20-trinor-;
13,14-didehydro-;
15-methyl-13,14-didehydro-;
16-methyl-13,14-didehydro-;
16,16-dimethyl-13,14-didehydro-;
16-fluoro-13,14-didehydro-;
16,16-difluoro-13,14-didehydro-;
17-phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
15-methyl-17-phenyl-18,19,20-trinor-13,14-didehydro-;
16-methyl-17-phenyl-18,19,20-trinor-13,14-didehydro-;

16,16-dimethyl-17-phenyl-18,19,20-trinor-13,14-didehydro-;
16-fluoro-17-phenyl-18,19,20-trinor-13,14-didehydro-;
16,16-difluoro-17-phenyl-18,19,20-trinor-13,14-didehydro-;
16-phenoxy-17,18,19,20-tetranor-13,14-didehydro-;
16-(m-trifluoromethylphenoxy)-17,18,19,20-tetranor-13,14-didehydro-;
16-(m-chlorophenoxy)-17,18,19,20-tetranor-13,14-didehydro-;
15-methyl-16-phenoxy-17,18,19,20-tetranor-13,14-didehydro-;
16-phenoxy-18,19,20-trinor-13,14-didehydro-;
15-methyl-16-phenoxy-18,19,20-trinor-13,14-didehydro-;
16-methyl-16-phenoxy-18,19,20-trinor-13,14-didehydro-;
13,14-dihydro-;
15-methyl-13,14-dihydro-;
16-methyl-13,14-dihydro-;
16,16-dimethyl-13,14-dihydro-;
16-fluoro-13,14-dihydro-;
16,16-difluoro-13,14-dihydro-;
15-methyl-16,16-difluoro-13,14-dihydro-;
17-phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
15-methyl-17-phenyl-18,19,20-trinor-13,14-dihydro-;
16-methyl-17-phenyl-18,19,20-trinor-13,14-dihydro-;
16,16-dimethyl-17-phenyl-18,19,20-trinor-13,14-dihydro-;
16-fluoro-17-phenyl-18,19,20-trinor-13,14-dihydro-;
16,16-difluoro-17-phenyl-18,19,20-trinor-13,14-dihydro-;
16-phenoxy-17,18,19,20-tetranor-13,14-dihydro-;
15-methyl-16-phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
15-methyl-16,16-difluoro-17-phenyl-18,19,20-trinor-13,14-dihydro-;
16-phenoxy-18,19,20-trinor-13,14-dihydro-;
15-methyl-16-phenoxy-18,19,20-trinor-13,14-dihydro-;
16-methyl-16-phenoxy-18,19,20-trinor-13,14-dihydro-;
cis-13-;
15-methyl-cis-13-;
16-methyl-cis-13-;
16,16-dimethyl-cis-13-;
16-fluoro-cis-13-;
16,16-difluoro-cis-13-;
15-methyl-16,16-difluoro-cis-13-;
17-phenyl-18,19,20-trinor-cis-13-;
17-(m-trifluoromethylphenyl)-18,19,20-trinor-cis-13-;
17-(m-chlorophenyl)-18,19,20-trinor-cis-13-;
17-(p-fluorophenyl)-18,19,20-trinor-cis-13-;
15-methyl-17-phenyl-18,19,20-trinor-cis-13-;
16-methyl-17-phenyl-18,19,20-trinor-cis-13-;
16,16-dimethyl-17-phenyl-18,19,20-trinor-cis-13-;
16-fluoro-17-phenyl-18,19,20-trinor-cis-13-;
16,16-difluoro-17-phenyl-18,19,20-trinor-cis-13-;
15-methyl-16,16-difluoro-17-phenyl-18,19,20-trinor-cis-13-;
16-phenoxy-17,18,19,20-tetranor-cis-13-;
16-(m-trifluoromethylphenoxy)-17,18,19,20-tetranor-cis-13-;
16-(m-chlorophenoxy)-17,18,19,20-tetranor-cis-13-;
16-(p-fluorophenoxy)-17,18,19,20-tetranor-cis-13-;
15-methyl-16-phenoxy-17,18,19,20-tetranor-cis-13-;
16-phenoxy-18,19,20-trinor-cis-13-;
15-methyl-16-phenoxy-18,19,20-trinor-cis-13-;
16-methyl-16-phenoxy-18,19,20-trinor-cis-13-;
15-methyl-16-phenoxy-18,19,20-trinor-cis-13-;
16-methyl-16-phenoxy-18,19,20-trinor-cis-13-;

EXAMPLE 5

2-Decarboxy-2-hydroxymethyl-5,6-trans-didehydro-9-deoxy-9-methylene-PGF$_1$

Following the procedure of Example 6 of U.S. Pat. No. 4,060,534, the methyl ester corresponding to the title product of Example 1 is transformed to the title product of the present example.

Further following the procedure of Example 5 there are prepared the various 2-decarboxy-2-hydroxymethyl-5,6-trans-didehydro-9-deoxy-9-methylene-PGF-type compounds corresponding to each of the various methyl esters described above.

EXAMPLE 6

2-Decarboxy-2-aminomethyl-5,6-trans-didehydro-9-deoxy-9-methylene-PGF$_1$

Following the procedure of Example 7 of U.S. Pat. No. 4,060,534, the methyl ester corresponding to the title product of Example 1 is transformed to the title product of the present example.

Further following the procedure of Example 4, there are prepared the various 2-decarboxy-2-aminomethyl-5,6-trans-didehydro-9-deoxy-9-methylene-PGF-type compounds corresponding to each of the various methyl esters described above.

FORMULAS

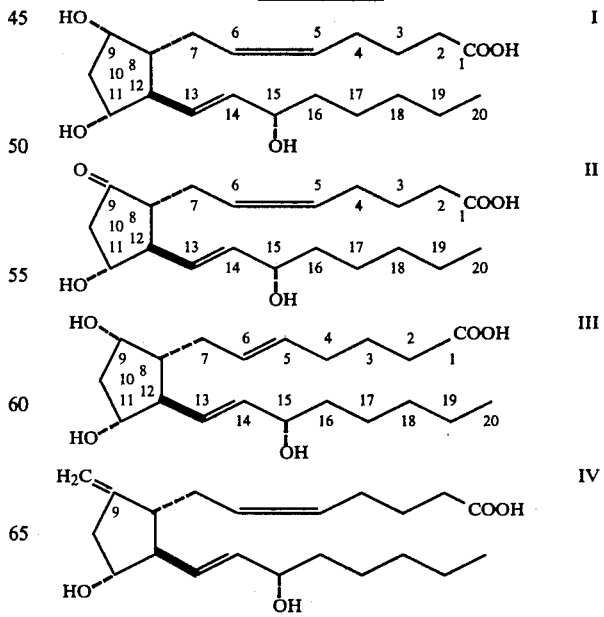

-continued
FORMULAS

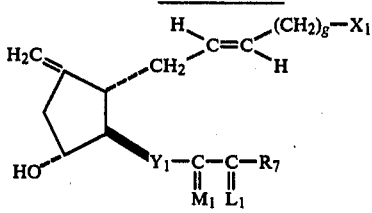

I claim:
1. A prostaglandin analog of formula VI

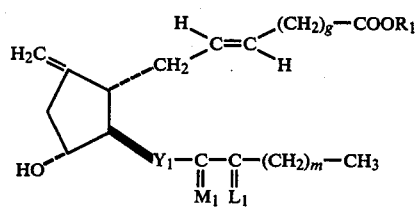

wherein $Y_1$ is trans-CH=CH—, —C≡C—, —CH$_2$CH$_2$—, or cis-CH=CH—;
wherein $M_1$ is α-$R_5$:β-OH or α-OH:β-$R_5$, wherein $R_5$ is hydrogen or methyl;
wherein $L_1$ is α-$R_3$:β-$R_4$, α-$R_4$:β-$R_3$, or a mixture of α-$R_3$:β-$R_4$ and α-$R_4$:β-$R_3$, wherein $R_3$ and $R_4$ are hydrogen, methyl or fluoro, being the same or different, with the proviso that one of $R_3$ and $R_4$ is fluoro only when the other is hydrogen or fluoro;
wherein g is 3, 4, or 5;
wherein m is an integer from one to 5, inclusive;
wherein $R_1$ is
 (a) hydrogen;
 (b) alkyl of one to 12 carbon atoms, inclusive;
 (c) cycloalkyl of 3 to 10 carbon atoms, inclusive;
 (d) aralkyl of 7 to 12 carbon atoms, inclusive;
 (e) phenyl;
 (f) phenyl substituted with one, two or three chloro or alkyl of one to 3 carbon atoms;
 (g) phenyl substituted in the para position by
  (i) —NH—CO—$R_{25}$
  (ii) —CO—$R_{26}$
  (iii) —O—CO—$R_{27}$
  (iv) —CH=N—NH—CO—NH$_2$
wherein $R_{25}$ is methyl, phenyl, acetamidophenyl, benzamidophenyl, or —NH$_2$; $R_{26}$ is hydroxy, methyl, phenyl, —NH$_2$ or methoxy; and $R_{27}$ is phenyl or acetamidophenyl; inclusive, or a pharmacologically acceptable salt thereof when $R_1$ is hydrogen.

2. A prostaglandin analog according to claim 2, wherein m is not 3.

3. A prostaglandin analog according to claim 2, wherein m is 3.

4. A prostaglandin analog according to claim 3, wherein g is 3.

5. A prostaglandin analog according to claim 4, wherein $Y_1$ is —C≡C—.

6. 5,6-trans-Didehydro-9-deoxy-9-methylene-13,14-didehydro-PGF$_1$, a prostaglandin analog according to claim 5.

7. A prostaglandin analog according to claim 4, wherein $Y_1$ is —CH$_2$CH$_2$—.

8. 5,6-trans-Didehydro-9-deoxy-9-methylene-13,14-dihydro-PGF$_1$, a prostaglandin analog according to claim 7.

9. A prostaglandin analog according to claim 4, wherein $Y_1$ is trans—CH=CH—.

10. A prostaglandin analog according to claim 9, wherein at least one of $R_3$ and $R_4$ is fluoro.

11. 5,6-trans-Didehydro-9-deoxy-9-methylene-16,16-difluoro-PGF$_1$, a prostaglandin analog according to claim 10.

12. A prostaglandin analog according to claim 9, wherein at least one of $R_3$ and $R_4$ is methyl.

13. 5,6-trans-Didehydro-9-deoxy-9-methylene-16,16-dimethyl-PGF$_1$, a prostaglandin analog according to claim 12.

14. 5,6-trans-Didehydro-9-deoxy-9-methylene-16,16-dimethyl-PGF$_1$, methyl ester, a prostaglandin analog according to claim 12.

15. A prostaglandin analog according to claim 9, wherein $R_3$ and $R_4$ are both hydrogen.

16. A prostaglandin analog according to claim 15, wherein $R_5$ is methyl.

17. 5,6-trans-Didehydro-9-deoxy-9-methylene-15-methyl-PGF$_1$, a prostaglandin analog according to claim 16.

18. A prostaglandin analog according to claim 15, wherein $R_5$ is hydrogen.

19. 5,6-trans-Didehydro-9-deoxy-9-methylene-PGF$_1$, methyl ester, a prostaglandin analog according to claim 18.

20. 5,6-trans-Didehydro-9-deoxy-9-methylene-PGF$_1$, a prostaglandin analog according to claim 18.

* * * * *

UNITED STATES PATENT OFFICE
CERTIFICATE OF CORRECTION

Patent No. 4,220,796                    Dated 2 September 1980

Inventor(s) Gordon L. Bundy

It is certified that error appears in the above-identified patent and that said Letters Patent are hereby corrected as shown below:

Column 1, line 32, "comound" should read -- compound --; line 50, "-C≡C-" should read -- -C≡C-;
Column 4, line 17, "-C≡C-" should read -- -C≡C- --;
Column 5, line 55, "2-phenylethylamide, 2-phenylethylamide," should read -- 2-phenylmethylamide, 2-phenylethylamide, --;
Column 8, line 36, "2-dluoro-" should read -- 2-fluoro- --; line 52, "or 2,3,5-)trimethylphenyl-" should read -- or 2,4,5-)trimethylphenyl- --;
Column 18, lines 4 and 6, "according to claim 2" should read -- according to claim 1 --; line 11, "-C≡C-" should read -- -C≡C- --.

Signed and Sealed this

Twenty-first Day of April 1981

[SEAL]

Attest:

RENE D. TEGTMEYER

Attesting Officer          Acting Commissioner of Patents and Trademarks